United States Patent

Monkovic et al.

[11] Patent Number: 5,173,486
[45] Date of Patent: Dec. 22, 1992

[54] DIBENZ[B,F][1,4]OXAZEPIN-11(10H)-ONES FOR MULTIDRUG RESISTANCE REVERSING AGENTS

[75] Inventors: Ivo Monkovic, Durham; Lotte Wang, North Haven, both of Conn.

[73] Assignee: Bristol-Myers Squibb Company, New York, N.Y.

[21] Appl. No.: 749,741

[22] Filed: Aug. 26, 1991

[51] Int. Cl.$^5$ .................... A61K 31/55; C07S 267/20
[52] U.S. Cl. .................................. 514/211; 540/488
[58] Field of Search .......................... 540/488; 514/211

[56] References Cited

FOREIGN PATENT DOCUMENTS 1164579 9/1969 United Kingdom ................ 540/488

OTHER PUBLICATIONS

Nagarajan, et al., Structure-Activity Relationships in Sintamil ® Series, Indian Journal of Experimental Biology, 12, pp. 217-224 (1974).

Primary Examiner—Robert T. Bond
Attorney, Agent, or Firm—William T. Han

[57] ABSTRACT

This invention relates to a compound of formula I

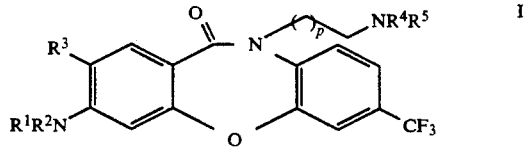

wherein
p is 1 to 3;
$R^1$ and $R^2$ each are independently hydrogen or an acyl group $R^6CO-$, in which $R^6$ is $C_{1-6}$ alkyl, $C_{3-7}$ cycloalkyl, $C_{2-7}$ alkenyl, aryl or radical of the formula

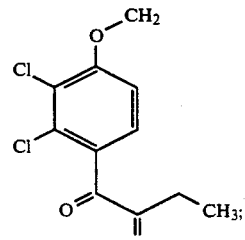

$R^3$ is hydrogen or chloro;
$R^4$ and $R^5$ each are independently $C_{1-6}$ alkyl.
Compounds of formula I are useful for the reversal of multidrug resistance of cancer drugs.

7 Claims, No Drawings

DIBENZ[B,F][1,4]OXAZEPIN-11(10H)-ONES FOR MULTIDRUG RESISTANCE REVERSING AGENTS

BACKGROUND OF INVENTION

1. Field of Invention

This invention relates to substituted dibenz[b,f][1,4]oxazepin-11(10H)-ones useful for the reversal of multidrug resistance of cancer cells to multiple cytotoxic drugs. Thus the compounds of the instant invention can be used for adjuvant chemotherapy for neoplasias resistant to multiple drugs.

2. Background of Related Art

The treatment of human tumors with cytotoxic drugs is an important part of the modern clinical cancer therapy. A major obstacle to effective cancer chemotherapy is the resistance of tumor cells to antineoplastic agents. Drug resistance in human malignancies may arise from multiple mechanisms. Of particular importance is the cross resistance of cancer cells to a diverse group of lipophilic drugs with unrelated structures and functions, a phenomenon known as multidrug resistance (MDR).

A common feature detected in all MDR cells in early studies was the reduction in intracellular steady state drug accumulation relative to sensitive cells. Later, it was discovered that this phenotype was frequently associated with the increased expression of a plasma membrane glycoprotein (P-gp) of 170kDa. The implication of this protein in MDR was confirmed by its ability to confer drug resistance through transfection of cloned P-gp gene (MDR-1) into sensitive cells. See: Grace Bradley, Peter F. Juranka & Victor Ling—Mechanisms of multidrug resistance, *Bioch. Biophys. Acta*,948, pp 87-128 (1988); Jane A. Endicott & Victor Ling - The biochemistry of P-glycoprotein-mediated multidrug resistance, *Ann. Rev. Biochem*, 58, pp 137-171 (1989); James M. Ford & William N. Hait—Pharmacology of drugs that alter multidrug resistance in cancer, *Pharmacological Reviews*. 42 , pp 155-199 (1990).

P-gp consists of two symmetrical halves, each has an ATP binding domain. Evidence suggests that it functions as an energy dependent pump with a broad range of substrate specificity. Relatively high levels of P-gp have also been found in certain normal human tissues, such as adrenal glands, kidney, colon and placenta. However, its physiological role and its natural substrate are as yet unclear. P-gp may serve to export naturally occurring toxins or xenobiotics as a detoxification mechanism. Surveys of clinical samples have found increased levels of P-gp in tumors derived from tissues which normally overexpress MDR-1 message. In addition, apparently, there is a direct correlation between the expression of P-gp with some drug refractory hematological malignancies and childhood soft tissue sarcomas, which do not normally express P-gp. See: Mace Rothenberg & Victor Ling—Multidrug Resistance: Molecular Biology and Clinical Relevance, *J. Nat. Cancer Inst.*, 81, pp 907-910, (1989); Helen S. L. Chan, Paul S. Thorner, George Haddad and Victor Ling—Immunohistochemical Detection of P-glycoprotein: Prognostic Correlation in Soft Tissue Sarcoma of Childhood, *J. Clin. Oncol.*, 8, pp 689-704 (1990). These findings support potential clinical role played by P-gp in both intrinsic and acquired MDR which ultimately render some cancer treatments inefficacious.

Several strategies have been devised to circumvent clinical MDR. One promising approach is the utilization of chemosensitizing agents which can inhibit active efflux of drugs in resistant cells. Numerous compounds including calcium antagonists, calmodulin inhibitors, and some drug analogues have shown variable abilities to reverse MDR. Most of these agents are lipophilic and may act as a substrate for the P-gp, thereby competitively inhibiting its drug efflux effect. Excellent reviews have recently been published on agents that alter multidrug resistance in cancer. See: James M. Ford & William N. Hait—Pharmacology of Drugs that Alter Multidrug Resistance in Cancer, *Pharmacological Reviews*, 42, pp 155-199 (1990); David J. Stewart & William K. Evans—Non-chemotherapeutic Agents that Potentiate Chemotherapy Efficacy, *Cancer Treatment Reviews*, 16, pp 1-40 (1989).

The major limiting factor to use certain MDR reversing agents in cancer patients so far is their toxicity which prevents them from reaching effective concentrations during treatment. Thus, challenge remains in the search of ideal MDR reversing agents which are more potent but less toxic and pharmacologically acceptable for clinical applications.

We have recently found a group of substituted dibenz[b,f][1,4]oxazepin-11(10H)-ones (hereinafter often abbreviated simply as oxapezines) with potent MDR reversing abilities. Oxazepines with structures somewhat related to those of the instant invention can be found, for example, in U.K. Patent No. 1,164,579 published Sept. 17, 1969, which discloses oxazepines of formula II

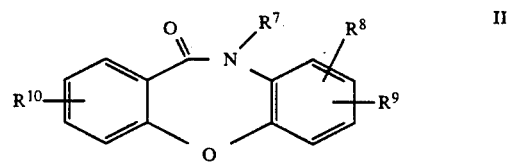

wherein $R^8$ is hydrogen or halogen, $R^7$ is hydrogen or $C_{1-6}$ alkyl, and one of $R^9$ and $R^{10}$ represents a free amino group whilst the other represents a hydrogen atom. Oxazepines of the formula II are reported to have analgesic, antipyretic, and sedative properties. Furthermore, Nagarajan et al. in the *Indian Journal of Experimental Biology*, 12, pp 217-224, at p 229, (1974), disclose oxazepine of formula III. Compound of formula III was made by the intramolecular cyclization of compound of formula IV in hot DMF.

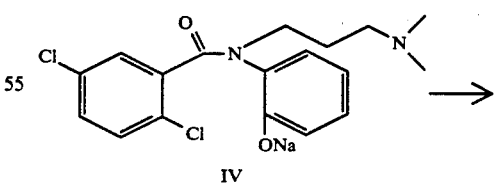

IV

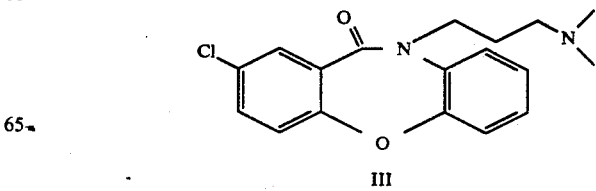

III

Analogous methods have been employed to make oxazepines of formula II above.

Neither oxazepines of formula II or III have been identified to have MDR reversing activities.

SUMMARY OF THE INVENTION

This invention relates to dibenz[b,f][1,4]-oxazepin-11(10H)-ones of formula I or a pharmaceutically acceptable salt thereof

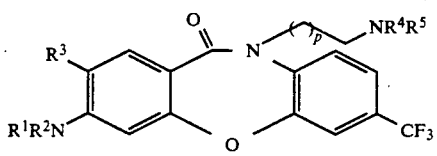

wherein p is 1 to 3;

$R^1$ and $R^2$ each are independently hydrogen or an acyl group $R^6CO$-, in which $R^6$ is $C_{1-6}$ alkyl, $C_{3-7}$ cycloalkyl, $C_{2-7}$ alkenyl, aryl or radical of the formula

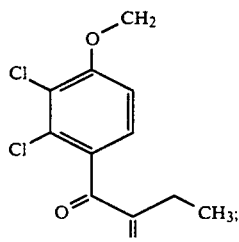

$R^3$ is hydrogen or chloro;

$R^4$ and $R^5$ each are independently $C_{1-6}$ alkyl.

Compounds of formula I are useful for the reversal of multidrug resistance of cancer drugs. Thus in another aspect, this invention relates to the use of compound of formula I as agents for adjuvant chemotherapy for neoplasias resistant to multiple drugs.

DETAILED DESCRIPTION OF THE INVENTION

This invention relates to dibenz[b,f][1,4]-oxazepine-11(10H)-ones of formula I or a pharmaceutically acceptable salt thereof

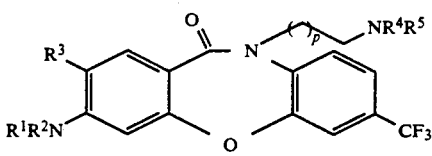

wherein p is 1 to 3;

$R^1$ and $R^2$ each are independently hydrogen or an acyl group $R^6CO$—, in which $R^6$ is $C_{1-6}$ alkyl, $C_{3-7}$ cycloalkyl, $C_{2-7}$ alkenyl, aryl or radical of the formula

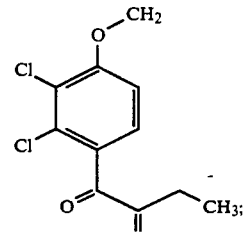

$R^3$ is hydrogen or chloro;

$R^4$ and $R^5$ each are independently $C_{1-6}$ alkyl.

Preferred compounds of formula I are those in which p equals 1, —$COR^6$ is a radical selected from

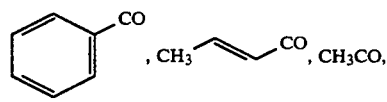

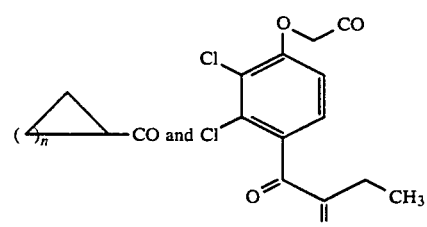

in which n is 1 to 4.

Compounds of formula I' (Scheme A), which form a subset of compounds of formula I wherein $R^1$ and $R^2$ are hydrogen and $R^3$ is Cl, can be made via many procedures. A preferred process is shown in Scheme A.

In Step 1 of Scheme A, the phenolic hydrogen in a compound of formula V is exchanged with a cation M to form a compound of formula VI. Examples of the cation include sodium, potassium, tetrabutylammonium, and benzyltriethylammonium, to name a few. This exchange may be effected with a base such as potassium carbonate, potassium hydroxide, potassium hydride, sodium hydride, sodium hydroxide, sodium carbonate, or a quaternary ammonium hydroxide such as tetrabutylammonium hydroxide or benzyltriethylammonium hydroxide. The reaction is usually conducted in an inert organic solvent such as acetone, acetonitrile, methylene chloride, dimethylformamide (DMF), dimethylacetamide, methanol, 2-methoxyethanol, ethanol, isopropanol, or diglyme.

Step 2 of Scheme A is effected by reacting the resultant phenolic salt of formula VI with a compound of formula VII, in which Y is a halogen, preferably fluoro or chloro. The addition is conducted in the presence of base such as potassium carbonate and in an inert organic solvent such as acetonitrile, DMF, dimethylacetamide, 2-methoxyethanol, ethanol, isopropanol, or diglyme. The preferred solvent is n-propanol, 2-methoxyethanol or DMF. And even more preferred solvent is 2-methoxyethanol. The reaction takes place at an elevated temperature, and even more preferably at the reflux temperature of the solvent used.

If desired, a compound of formula I' can be monoacylated or di-acylated at the free 3-amino group to replace one or two hydrogen atoms with the same or different $R^6CO$— radicals which have the meaning as defined earlier. The acylation technique for a free aromatic amine is well established in the art. For example, for mono-acylation, a compound of formula I' can be coupled with an equimolar amount of acid R⁶COOH in the presence of a dehydrating agent such as dicyclohexylcarbodiimide or 1-ethoxycarbonyl-2-ethoxy-1,2-dihydroquinoline (EEDQ). Other dehydrating agents such as the ones which appear in *Synthesis*, pp 453-463 (1972) may also be suitable. Alternatively, the carboxy group of R⁶COOH can be converted to a reactive derivative which can be used in the N-acylation. Reactive derivatives of the carboxy group that can be used are acid halides; acid imidazolides; acid azides; mixed acid anhydrides; active esters such as those formed with ethyl chloroformate or isobutyl chloroformate; phenylcarbamates; N-hydroxyimides such as formed with N-hydroxysuccinimide or N-hydroxyphthalimide; and those formed with hydroxybenzotriazole (HBT) or 4-methyltetrazole-5-thione; or like active carboxy derivatives. In forming a compound of formula I in which $R^1$ and $R^2$ are the same acyl groups, at least two equivalents of the same acylating reagents should be employed. On the other hand, when two different acyl groups are desired, the acylation is preferably conducted stepwise with different acylating reagents.

In forming a compound of formula I, in which $R^3$ is hydrogen, the 2-chloro group of a compound of formula I' can be hydrogenolized and, if desired, the free 3-amino group acylated as described above. Alternatively, a compound of formula I' is first acylated and subsequently the 2-chloro group is hydrogenolized.

The synthesis of a class of compounds of formula V is well described in several patent literatures and publications. More convenient processes are those which have been used to make the starting materials for the compounds patented in U.S. Pat. No. 4,808,624. Other processes which may be adopted to make compounds of formula V are summarized in the Complete Disclosure section of the same U.S. Patent.

In another embodiment, a series of steps as shown in Scheme B may be employed to obtain a compound of formula I''. In the scheme, $R^1$ and $R^2$ in a compound of formula IX have the meaning as defined previously. Thus when $R^1$ and $R^2$ are both hydrogen, Step 1 is not carried out. Preferably, however, at least either $R^1$ or $R^2$ is an acyl group R⁶CO— which has the earlier defined meaning. Even more preferably, either one of $R^1$ or $R^2$ is an acetyl group whilst the other is hydrogen.

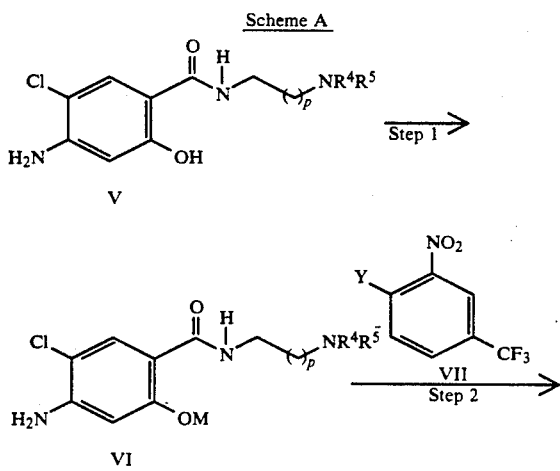

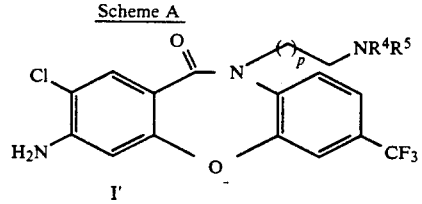

The acetyl group can serve as a protecting group which can be easily removed by base hydrolysis in a later step. The mono- or di-acylation in Step 1 can be effected by the procedures analogous to the ones described for compounds of formula I'.

The carboxy group in a compound of formula IX is protected with a conventional carboxy protecting group $R^{11}$ in Step 2. Conventional carboxy protecting groups which can be employed in the present invention to block or protect the carboxylic acid function are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxy-protecting groups include moieties such as $C_{1-6}$ alkyl, diphenylmethyl (benzyhydryl), 2-naphthylmethyl, 4-pyridylmethyl, phenacyl, acetonyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl $C_{1-6}$ alkyl, ring substituted phenyl $C_{1-6}$ alkyl, e.g., benzyl, 4-methoxybenzyl, 4-nitrobenzyl (p-nitrobenzyl), 2-nitrobenzyl (o-nitrobenzyl), and triphenylmethyl (trityl), methoxymethyl, 2,2,2-trichloroethoxycarbonyl, benzyloxymethyl, $C_{1-6}$ alkanoyloxy $C_{1-6}$ alkyl such as acetoxymethyl, propionyloxymethyl, $C_{2-6}$ alkenyl such as vinyl and allyl. Other suitable carboxy protecting groups well known in the art which have not been disclosed above can be found in "Protective Groups in Organic Synthesis", Theodora W. Greene (John Wiley & Sons, 1981), Chapter 5 incorporated herein by reference. As used herein, the particularly advantageous carboxy protecting group is allyl.

In step 3, the free phenolic hydrogen is exchanged with a cation M by a procedure analogous to that described for Step 1 of Scheme A. A compound of formula XI thus formed is reacted with a compound of formula VII in Step 4 to afford a compound of formula XII wherein radical W stands for

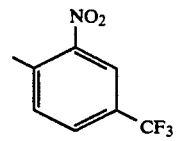

The conditions employed in Step 4 are analogous to those employed for Step 2 in Scheme A.

Step 5 involves removal of a conventional carboxy protecting group. When $R^{11}$ is allyl, it can be removed with tris(dibenzylideneacetone)dipalladium (0) and triphenylphosphine.

Step 6 involves condensation of an amine H₂NCH₂(CH₂)ₚNR⁴R⁵ with a benzoic acid derivative of formula XIII to afford a benzamide of formula XIV and subsequent base promoted rearrangement to a compound of formula XV. Several methods are available to form benzamides from primary amines and benzoic acid derivatives of the type shown as formula XIII. For example, the Complete Disclosure section of U.S. Pat. No. 4,808,624 outlines a few representative procedures. Benzamides of formula XIV are not normally isolated but are immediately converted by base such as potassium carbonate to a compound of formula XV.

Upon heating, preferably at the reflux temperature of the solvent used, a benz[b,f][1,4]oxazepine of formula I" is obtained in Step 7. Preferable solvent is one which does not interfere with the intramolecular cyclization; examples include acetonitrile, 2-methoxyethanol, dimethylacetamide, methanol, isopropanol, or diglyme. Particularly preferred solvent is 2-methoxyethanol.

If desired, a compound of formula I" can be chlorinated at the 2-position in Step 8. The chlorination can be achieved by a standard manner of chlorinating an aromatic ring such as by sulfuryl chloride in methylene chloride, chlorine in acetic acid, N-chlorosuccinimide, or other suitable methods of chlorination.

When $R^1$ and $R^2$ are hydrogen and acetyl, the acetyl group can be removed by base hydrolysis to afford a compound of formula I" or I'" wherein —$NR^1R^2$ is a free amino group which can be mono- or di-acylated with $R^6CO$— radicals if desired to afford further compounds within the scope of this invention.

Scheme B

VIII

IX

I

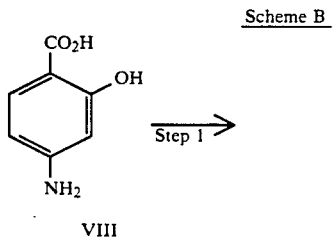

XI

-continued
Scheme B

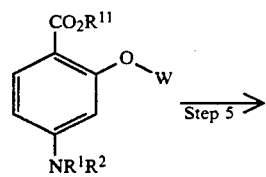

XII

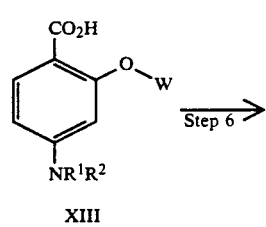

XIII

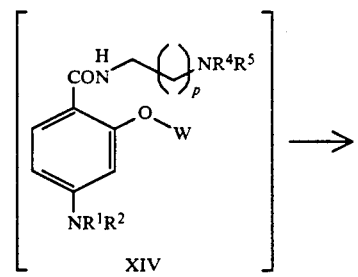

XIV

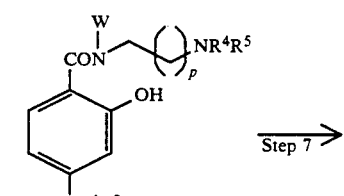

XV

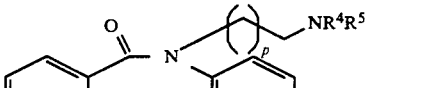

I"

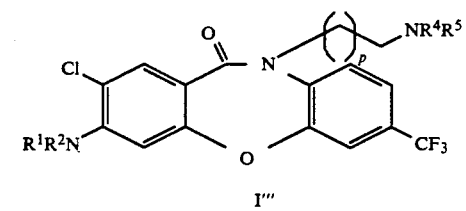

I'"

In the instant application, the numbers in subscript after the symbol "C" define the number of carbon atoms a particular group can contain. For example, $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl and the like alkyl groups; $C_{2-6}$ alkenyl refers to straight or branched alkenyl groups such as vinyl, allyl, 1-propenyl, isopropenyl, 1-butenyl, 2-butenyl, methallyl, 1,1-dimethylallyl, 1-hexenyl 2-hexenyl and the like groups; cyclic $C_{3-7}$ alkyl refers to groups such as cyclopropyl, cyclobutyl, cyclopentyl, cyclohexyl, cylcoheptyl, cyclopropylmethyl, cyclopropylethyl, cyclopropylpropyl, cylcobutylmethyl, cyclobutylethyl, cyclopentylmethyl and the like groups; aryl group refers to unsubstituted phenyl or phenyl independently substituted with one to three halogen, $C_{1-6}$ alkyl, $C_{1-6}$ dimethoxyphenyl, 2-methyl-3-ethoxylphenyl, 4-t-butoxyphenyl, 4-methylthio-3-fluorophenyl, 2,4-dichlorophenyl, 2-chloro-4-bromophenyl and the like groups; $C_{1-6}$ alkyloxy (alkoxy) refers straight or branched alkyloxy groups such as methoxy, ethoxy, n-propoxy, i-propoxy, n-butoxy, t-butoxy, n-pentyloxy, n-hexyloxy, 3-methylpentyloxy, to name a few; $C_{1-6}$ alkylthio refers straight or branched alkylthio groups such as methylthio, ethylthio, n-propylthio, i-propylthio, n-butylthio, t-butylthio, n-pentylthio, n-hexylthio, 3-methylpentylthio and the like groups; and halogen refers to fluorine, chlorine, bromine, or iodine.

The structural formulae as drawn herein are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

DESCRIPTION OF SPECIFIC EMBODIMENTS

The specific examples which follow illustrate the synthesis of representative compounds of the instant invention and are not construed as limiting the invention in sphere or scope. The methods may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), D$_2$O (deuterated water), CDCl$_3$ (deuterochloroform) and other conventional deuterated solvents. The infrared (IR) spectral description include only absorption wave numbers (cm$^{-1}$) having functional group identification value.

Celite is a registered trademark of the Johns-Manville Products Corporation for diatomaceous earth.

The abbreviations used herein are conventional abbreviations widely employed in the art. Some of which are:
MS: Mass spectrometry
HRMS: High resolution mass spectrometry
DMF: Dimethylformamide
Ac: Acetyl
ADR: Adriamycin
ActD: Actinomycin D
DMSO: dimethyl sulfoxide
Ph: phenyl

EXAMPLE 1

3-amino-2-chloro-10-2-(diethylamino)ethyl]-7-(trifluoromethyl)
dibenz[b,f][1,4]oxazepin-11(10H)-one (Ia)

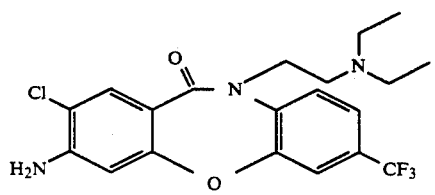

A suspension of 60% sodium hydride in mineral oil (1.76 g, 44 mmol, washed with n-pentane) under nitrogen was treated with n-propanol (80 ml). To this was added 4-amino-5-chloro-N-[2-(diethylamino)ethyl]-2-hydroxybenzamide hydrochloride (6.44 g, 20 mmol) and 4-chloro-3-nitrobenzotrifluoride (4.51 g, 20 mmol). The mixture was heated under reflux for 6 h and then concentrated in vacuo. The residue was partitioned between aqueous NaHCO$_3$ solution and a 1:1:1 mixture of dichloromethane, ether and n-hexane. The organic phase was washed with 1N NaOH, water and than treated with 20 ml of 1N HCl. A precipitated solid was collected by filtration and washed with acetone to give 1.65 g of crude 3-amino-2-chloro-10-[2-(diethylamino) ethyl]-7-(trifluoromethyl)dibenz[b,f]-[1,4]oxazepin-11(10H)-one (Ia) dihydrochloride, as a light yellow solid. The mother liquors were combined, neutralized with an aqueous solution of NaHCO$_3$ and extracted into CH$_2$Cl$_2$. The extract was dried and concentrated and the residue was chromatographed on silica using CH$_2$Cl$_2$ with 2–8% MeOH as the eluent, to give the following three fractions.

a) The first fraction was 430 mg of 4-amino-5-chloro-N-[2-(diethylamino) ethyl]-N-[2-nitro-4-(trifluoromethyl)phenoxy]benzamide obtained as a yellow amorphous solid, mp >60° C.

$^1$H NMR (CDCl$_3$) $\delta$8.0–8.3 (m, 3H), 7.7–7.9 (m, 4H), 7.02 (s, 1H), 6.11 (s, 1H), 4.26 (m, 2H), 2.2–2.8 (m, 6H), 0.80 (m, 6H);

MS(m/e) 663;

Anal, Calcd for C$_{27}$H$_{24}$ClF$_6$N$_5$O$_6$: C 48.84, H 3.64, N 10.55 Found: C 50.75, H 4.00, N 9.85.

b) The second fraction was 359 mg of 3-amino-2-chloro-10-[2-(diethylamino)ethyl]-7-(trifluoromethyl)-dibenz[bf][1,4]oxazepin-11(10H)-one (Ia) obtained as a free base.

$^1$H NMR (CDCl$_3$) $\delta$7.72 (s, 1H), 7.63 (d, 1H), 7.42 (d, 1H), 4.42 (s, 1H), 6.52 (s, 1H), 4.45 (s, 2H), 4.09 (+2H), 2.77 (t, 3H), 2.52 (q, 4H), 6.96 (t, 6H);

Ms (m/e) 428 corresponds to M+H$^+$.

The sample was treated with anhydrous HCl in MeOH, and the product was combined with previously obtained solid (1.65 g) and recrystallized from MeO-HEt₂O to give 1.85 g of a light beige solid, mp >130° C.

Analysis, Calcd for C₂₀H₂₁ClF₃N₃O₂.2 HCl: C 47.97, H 4.63, N 8.39 Found: C 47.74, H 4.58, N 8.33.

c) The third fraction was 68 mg of 4-amino-5-chloro-N-[2-(diethylamino)ethyl]-2-hydroxy-N-[2-nitro-4-(trifluoromethyl)phenyl]benzamide obtained as a yellow solid, mp >100° C.

¹H NMR (CDCl₃) δ8.10 (s, 1H), 7.96 (s, 2H), 6.38 (s, 1H), 6.21 (s, 1H), 4.39 (s, 2H), 4.2–4.4 (m, 2H), 2.7–3.2 (m, 6H), 1.2 (m, 6H);

MS (m/e) 474.

In another experiment 3-amino-2-chloro-10-[2-(diethylamino)ethyl]-7-(trifluoromethyl)-dibenz[b,f][1,4]oxazepin-11(10H)-one dihydrochloride was prepared as follows: A mixture of tetrabutylammonium salt of 4-amino-5-chloro-N-[2-(diethylamino)ethyl]-2-hydroxybenzamide (13.182 g, 25 mmol), K₂CO₃ (1.73 g, 12.5 mmol) and 4-chloro-3-nitrobenzotrifluoride (5.63 g, 25 mmol) in 100 ml of n-propanol was refluxed for 14 h and than concentrated in vacuo. The residue was partitioned between aqueous Na₂CO₃ and ethyl acetate (300 ml). The organic phase was washed with 3×200 ml water, 0.5 N aqueous NaOH (50 ml), water and than treated with n-pentane until dark brown droplets separated. The supernatant was decanted and treated with 30 ml of 2N hydrochloric acid causing precipitation. The solid was collected by filtration and washed with ethyl acetate to give after drying 5.84 g, (46.6%) of the title compound as a dihydrochloride.

In yet another experiment, a mixture of tetrabutylammonium salt of 4-amino-5-chloro-N-[2-(diethylamino)ethyl]-2-hydroxybenzamide (52.73 g), 4-chloro-3-nitrobenzotrifluoride (22.56 g. 0.1 mol) and K₂CO₃ (6.92 g, 50 mmol) in 300 ml of 2-methoxyethanol was stirred and heated at reflux for 17 h. The mixture was concentrated in vacuo and the residue partitioned between water and ethyl acetate. The organic phase was washed with 2×50 ml of 1 N NaOH, 2×100 ml of water, and then treated with 50 ml of 2 N HCl. A solid precipitate was collected by filtration and washed with CH₂Cl₂ and ethyl acetate to give after drying on air 29.44g (58.9 %) of dihydrochloride salt of the title compound.

EXAMPLE 2

N-2-Chloro-10,11-dihydro-10-[2-(diethylamino)ethyl-11-oxo-7-(trifluoro methyl) dibenz[b,f][1,4]oxazepin-3-yl]acetamide (Ib) and N-acetyl-N-[2-chloro-10,11-dihydro-10-[2-(diethylamino) ethyl-11-oxo-7-(tri-fluoromethyl) dibenz[b,f][1,4]oxazepin-3-yl]acetamide (Ic)

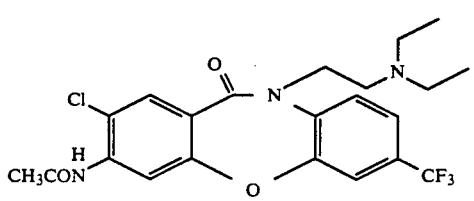
Ib

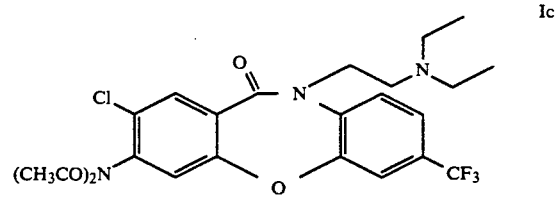
Ic

A solution of compound Ia in 10 ml acetic anhydride was heated to reflux for 12 min and then concentrated in vacuo. The residue was chromatographed on silica gel using dichloromethane with 1–5% methanol as the eluent to give first 295 mg of compound Ic as a yellow amorphous solid.

¹H NMR (CDCl₃) δ 7.97 (s, 1H), 7.72 (d, 1H), 7.49 (d, 1H), 7.45 (s, 1H), 7 13 (s, 1H), 4.2 (t, 2H), 2.89 (t, 2H);

MS (m/e) 511. 820 mg of monoacetylated product Ib was obtained next as a beige solid, mp 143°–4° C.

Anal. Calcd for C₂₂H₂₃ClF₃N₃O₃.0.5H₂O.0.5CH₃CO₂H: C 54.31; H 5.06; N 8.27. Found: C 54.68; H 5.11; N 7.93.

¹H NMR (CDCl₃) δ 8.43 (s, 1H), 7.82 (s, 1H), 7 74 (s, 1H), 7.63 (d, 1H), 7.52 (s, 1H), 7.44 (d, 1H), 4.18 (t, 2H), 2.87 (t, 3H), 2.63 (q, 4H), 2.26 (s, 3H), 2.02 (s, 2H), 1.02 (t, 6H);

MS(m/ⓔ) 469.

EXAMPLE 3

N-[10,11-dihydro-10-[2-(diethylamino)ethyl]-11-oxo-7-(trifluoromethyl)-dibenz[b.f][1,4]oxazepin-3-yl]acetamide (Id)

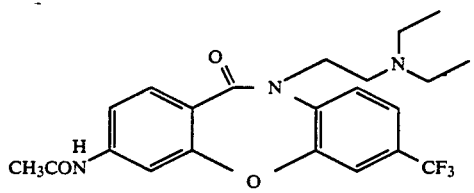

To a mixture of compound Ib (270 mg ) and ammonium formate (220 mg ) in 8 ml of methanol was added 10 mg of 10% Pd on carbon. This was stirred for 5 h and the catalyst was filtered off. The filtrate was concentrated in vacuo and the residue partitioned between aqueous NaHCO₃ and dichloromethane. The organic layer was dried and concentrated in vacuo to give 190 mg of the title compound as a white solid, mp 75–85° C.

¹H NMR (CDCl₃) δ 8.34 (s, 1H), 7.75 (d, 1H), 7.65 (t, 2H), 7.46 (s, 1H), 7.40 (dd, 1H), 7.10 (dd, 1H), 4.10 (t, 2H), 2.76 (t, 2H), 2.49 (q, 4H), 2.14 (s, 3H), 0.96 (t, 6H);

MS (m/e) 434;

HRMS Calcd for C₂₂H₂₄F₃N₃O₃ 436.1848. Found: 436.1846.

EXAMPLE 4

N-[2-Chloro-10,11-dihydro-10-[2-(diethylamino)ethyl-11-oxo-7-(trifluoromethyl)-dibenz[b.f][1,4]oxazepin-3-yl]benzamide (Ie)

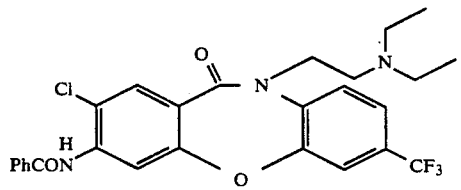

To a stirred solution of compound Ia (250 mg, 0.5 mmol) and triethylamine (102 mg, 1 mmol) in 2 ml of anhydrous CH$_2$Cl$_2$ was added benzoyl chloride (141 mg, 1 mmol). The mixture was stirred for 1 h and then was partitioned between aqueous sodium carbonate and CH$_2$Cl$_2$. The organic phase was dried, concentrated in vacuo and the residue chromatographed on silica gel using CH$_2$Cl$_2$ with 5 to 10% MeOH as the eluent to give 182 mg (68.3%) of the title compound as a yellow solid, mp 67°–69° C.

$^1$H NMR (CDCl$_3$) δ 8.55 (s, 1H), 7.90 (d, 1H), 7.55 (m, 8H), 4.05 (m, 2H), 2.72 (q, 2H), 2.50 (m, 5H), 0.96 (m, 6H);

HRMS Cald for C$_{27}$H$_{25}$ClF$_3$N$_3$O$_3$ 532.1615 Found: 532.1627

EXAMPLE 5

N-[2-Chloro-10,11-dihydro-10-[2-(diethylamino)ethyl-11-oxo-7-(trifluoromethyl)dibenz[b.f][1,4]oxazepin-3-yl]crotonamide (If)

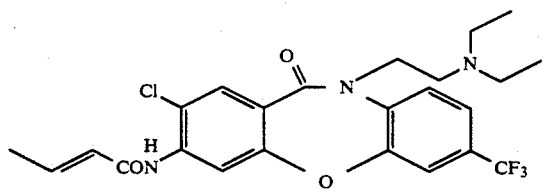

The general procedure for the preparation of compound Ie was repeated except that benzoyl chloride utilized therein was replaced by equimolar amount of crotonyl chloride. The yield of the title compound, a yellow solid, was 61.3%, mp 106°–107° C.

$^1$H NMR (CDCl$_3$) δ 8.50 (s, 1H), 7.87 (d, 1H), 7.55 (m, 2H), 7.00 (m, 2H), 5.82 (dd, 2H), 4.25 (m, 3H), 2.95 (m, 1H), 2.75 (m, 1H), 1.85 (q, 6H), 1.10 (m, 6H).

HRMS Calcd for C$_{24}$H$_{26}$N$_3$O$_3$F$_3$Cl 496.1615. Found: 496.1605.

EXAMPLE 6

[2-Chloro-10,11-dihydro-10-[2-(diethylamino)ethyl-11-oxo-7-(trifluoromethyl)dibenz[b.f][1,4]oxazeoin-3-yl]propionamide (Ig)

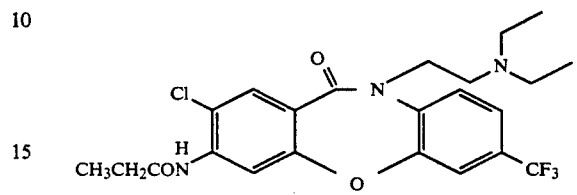

The general procedure for the preparation of compound Ie was repeated except that benzoyl chloride utilized therein was replaced with equimolar amount of propionyl chloride and the reaction time was 12 hrs. The title compound was obtained in 75.0% yield as a yellow oil.

$^1$H NMR (CDCl$_3$) δ 8.42 (s, 1H), 7.78 (s, 1H), 7.75 (s, 1H), 7.60 (d, 1H), 7.45 (d, 1H), 7.35 (dd, 1H), 4.10 (t, 2H), 2.80 (t, 2H), 2.45 (m, 6H), 1.25 (t, 3H), 0.95 (t, 6H).

HRMS Calcd for C$_{23}$H$_{26}$ClF$_3$N$_3$O$_3$ 484.1615. Found: 484.1612.

EXAMPLE 7

N-[2-Chloro-10,11-dihydro-10-[2-(diethylamino)ethyl-11-oxo-7-(trifluoromethyl)dibenz[b,f][1,4]oxazeoin-3-yl]cyclopropanecarboxamide (Ih)

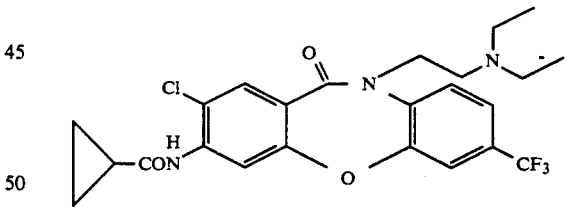

The general procedure for the preparation of compound Ie was repeated except that benzoyl chloride utilized therein was replaced by equimolar amount of cyclopropanecarbonyl chloride, and the reaction time was 12 h. The title compound was obtained in 80.7% yield as a yellow solid, mp 115–116° C.

$^1$H NMR (CDCl$_3$) δ 8.39 (s, 1H), 7.80 (s, 1H), 7.75 (s, 1H), 7.58 (d, 1H), 7.42 (s, 1H), 7.25 (q, 1H), 4.10 (t, 2H), 2.70 (t, 2H), 2.50 (q, 3H), 1.55 (m, 3H), 1.07 (s, 1H), 1.05 (m, 2H), 0.95 (t, 6H).

HRMS Calcd for C$_{24}$H$_{26}$ClF$_3$N$_3$O$_3$ 496.1615. Found: 496.1605.

EXAMPLE 8

N-[2-Chloro-10,11-dihydro-10-[2-(diethylamino)ethyl-11-oxo-7-(trifluoromethyl) dibenz[b,f]1,4]oxezpin-3-yl]-2-methylpropionamide (Ii)

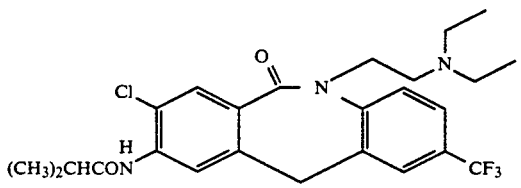

The general procedure for the preparation of compound Ie was repeated except that benzoyl chloride utilized therein was replaced with equimolar amount of isobutyril chloride and reaction time was 2 h. The title compound was obtained in 81.6% yield as a yellow solid, mp 73°-75° C.

$^1$H NMR (CDCl$_3$) δ 8.42 (s, 1H), 7.77 (s, 1H), 7.57 (m, 3H), 7.35 (s, 1H), 4.0 (m, 2H), 2.70 (t, 2H), 2.5 (m, 4H), 1.25 (d, 6H), 1.15 (s, 1H), 0.95 (m, 6H).

HRMS Calcd for C$_{24}$H$_{28}$ClF$_3$N$_3$N$_3$O$_3$ 498.1771. Found: 498.1761

EXAMPLE 9

N-[2-Chloro-10,11-dihydro-10-[2-(diethylamino)ethyl-11-oxo-7-(trifluoromethyl) dibenz[b,f][1,4]oxezpin-3-yl]cyclobutanecarboxamide (Ij)

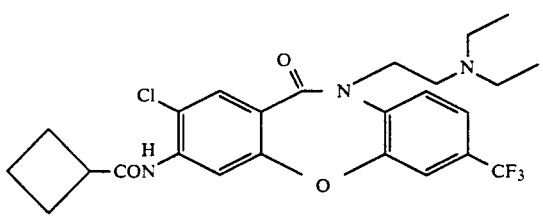

The general procedure for the preparation of compound (Ie) was repeated except that benzoyl chloride utilized therein was replaced with equimolar amount of cyclobutanecarbonyl chloride and the reaction time was 2h. The title compound was obtained in 54.3% yield as a yellow oil.

$^1$H NMR (CDCl$_3$) δ8.48 (s, 1H), 7.80 (s, 1H), 7.60 (m, 3H), 7.40 (m, 1H), 4.04 (m, 3H), 3.18 (m, 1H), 2.70 (t, 3H), b 2.48 (q, 4H), 2.30 (m, 3H), 1.98 (m, 1H), 0.97 (m, 6H).

The HRMS Calcd for C$_{25}$H$_{28}$ClF$_3$N$_3$O$_3$ 510.1771. Found: 510.1760.

EXAMPLE 10

N-[2-Chloro-10,11-dihydro-10-[2-(diethylamino)ethyl]-11-oxo-7-(trifluoromethyl) dibenz[b,f][1,4]oxazepin-3-yl]cyclohexacarboxamide (Ik)

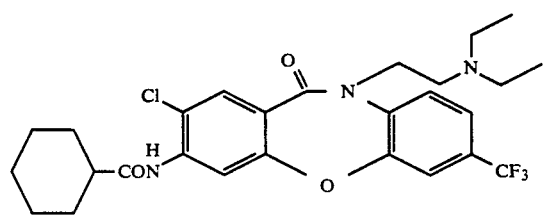

The general procedure for the preparation of comound Ie was repeated except that benzoyl chloride utilized therein was replaced with equimolar amount of cyclohexanecarboxylic acid chloride and the reaction time was 20 h. The title comound was obtained in 83% yield as a white solid, mp 137°-138° C.

$^1$H NMR (CDCl$_3$) δ8.50 (s, 1H), 7.87 (s, 1H), 7.86 (s, 1H), 7.68 (d, 1H), 7.55 (s, 1H), 7.47 (d, 1H), 4.15 (t, 2H), 2.82 (t, 2H), 2.56 (q, 4H), 2.35 (m, 1H), 1.2–2.1 (m, 10H), 1.00 (t, 6H).

HRMS Calcd for C$_{27}$H$_{31}$ClF$_3$N$_3$O$_3$ 538.2084. Found: 538.2076.

EXAMPLE 11

N-[2-Chloro-10,11-dihydro-10-[2-(diethylamino)ethyl]-11-oxo-7-(trifluoromethyl) dibenz[b,f][1,4]oxazepin-3-yl]-N-(cycloheptylcarbonyl) cycloheptanecarboxamide cycloheptanecarboxylate (Im) and
N-[2-chloro-10,11-dihydro-10-[2-(diethylamino) ethyl]-11-oxo-7-(trifluoromethyl) dibenz[b,f][1,4]oxazepin-3-yl]cycloheptanecarboxylate (In)

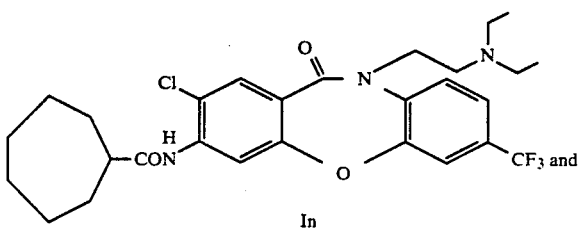

In

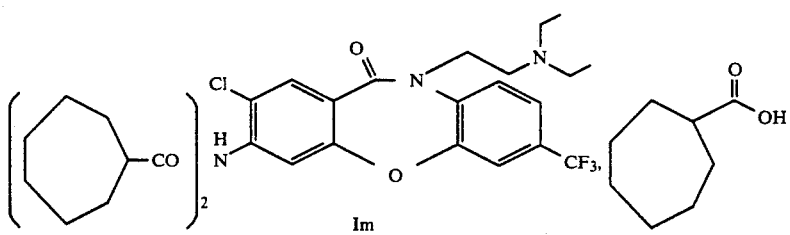 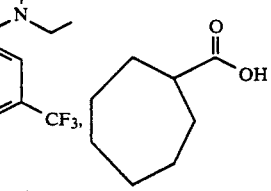

The cycloheptanecarbonyl chloride was prepared in situ by reaction of cycloheptanecarboxylic acid and oxalyl chloride in $CH_2Cl_2$ for 30 min. The excess oxalyl chloride was removed in vacuo. Thereafter, the general procedure for the preparation of compound Ie was repeated, except that benzoyl chloride utilized therein was replaced by cycloheptanecarbonyl chloride and the reaction time was 3 days. The product was purified on silica gel column using $CH_2Cl_2$ with 0.4% MeOH as the eluent, to give first compound Im (30%) as a yellow semisolid.

$^1$H NMR ($CDCl_3$) δ 7.90 (s, 1H), 7.74 (d, 1H), 7.42 (d, 1H), 7.41 (s, 1H), 7.01 (s, 1H), 4.08 (t, 2H), 2.75 (t, 3H), 2.48 (q, 4H), 2.23 (m, 2H), 1.1–2.0 (m, 36H), 0.91 (t, 6H).

HRMS Calcd for $C_{26}H_{45}ClF_3N_3O_4$ 676.3129. Found: 676.3115.

Continued elution of the column with $CH_2Cl_2$ with 1 to 4% MeOH as the eluent gave second fraction containing compound In in 43.9% yield as a white solid, mp 120°–125° C.

$^1$H NMR ($CDCl_3$) δ 8.40 (s, 1H), 7.78 (s, 1H), 7.72 (s, 1H), 7.59 (d, 1H), 7.47 (s, 1H), 7.30 (d, 2H), 4.08 (t, 2H), 2.75 (t, 2H), 2.47 (q, 4H), 2.41 (m, 1H), 1.4–2.1 (m, 12H), 0.93 (t, 6H).

HRMS Calcd for $C_{28}H_{33}ClF_3N_3O_3$ 552.2241. Found: 552.22413.

EXAMPLE 12

N-2-Chloro-10,11-dihydro-10-[2-(diethylamino)ethyl]-11-oxo-7-(trifluoromethyl) dibenz[b,f][1,4]oxazepin-3-yl]ethacrynylamide (Io)

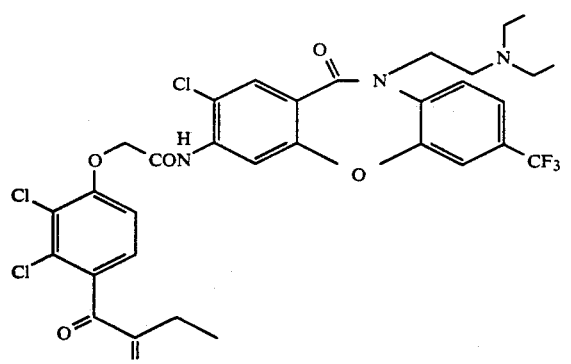

Ethacrynic acid (303 mg, 1 mmol) in 5 ml $CH_2Cl_2$ was activated by reaction with 0.5 N solution of chloromethylene-dimethylimmonium chloride in chloroform (Arnolds reagent) (2 ml, prepared by reaction of oxalyl chloride and DMF in chloroform) for 30 min. To this was added amine Ia (250 mg, 0.585 mmol) and triethylamine (153 mg, 1.5 mmol) and the mixture was stirred for 14 h. The reaction mixture was partitioned between aqueous $NaHCO_3$ and $CH_2Cl_2$. The organic layer was washed with water, dried and concentrated in vacuo. The residue was chromatographed on preparative silica gel plate using $CH_2Cl_2$ with 20% MeOH as a mobile phase to give 250 mg (69.8%) of the title compound as a yellow solid, mp 173°–175° C.

$^1$H NMR ($CDCl_3$) δ 8.46 (s, 1H), 7.80 (s, 1H), 7.62 (d, 1H), 7.50 (s, 1H), 7.40 (d, 1H), 7.10 (d, 2H), 6.85 (d, 1H), 5.90 (s, 1H), 5.55 (s, 1H), 4.70 (s, H), 4.07 (m, 2H), 2.85 (m, 1H), 2.60 (m, 3H), 2.40 (t, 2H), 1.10 (t, 3H), 1.0 (t, 6H).

HRMS Calcd for $C_{33}H_{32}ClF_3N_3O_3$ 712.1360. Found: 712.1346.

EXAMPLE 13

N-[2-Chloro-10,11-dihydro-10-[2-(diethylamino)ethyl-11-oxo-7-(trifluoromethyl) dibenz[b,f][1,4]oxazepin-3-yl]cyclopentanecarboxamide (Io)

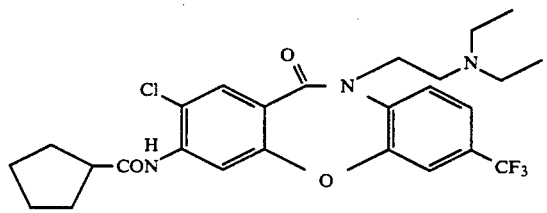

The general procedure for the preparation of compound Io was repeated except that ethacrynic acid utilized therein was replaced by cyclopentanecarboxylic acid in equimolar amount. The title compound was obtained in 58.3% as a yellow oil.

$^1$H NMR ($CDCl_3$) δ 8.45 (s, 1H), 7.81 (d, 2H), 7.7 (d, 1H), 7.50 (d, 1H), 7.42 (q, 1H), 4.15 (t, 2H), 2.80 (m, 4H), 2.55 (q, 5H), 1.85 (m, 5H), 1.65 (m, 1H), 0.95 (t, 6H);

HRMS Calcd for $C_{26}H_{30}N_3O_3F_3Cl$ 524.1928. Found: 524.1922.

EXAMPLE 14

4-Acetamidosalicylic acid (IXa)

To a stirred, refluxing suspension of 4-aminosalicylic acid (76.57 g, 0.5 mmol) in 250 mL absolute ethanol was added dropwise, over a 30 minute period, acetic anhydride (83.2 g, 0.815 mmol). After the addition was complete, the mixture was refluxed for another 15 minutes and then cooled. The product collected by filtration, washed with small amount of ethanol and dried on air to give 72.3 g (74.15%) of the title compound as a grey solid mp 242° 14 4° C. Previously reported mp: 234°–5° C. (P. Barraclough et al. *Eur. J. Chem.* 25, p 467, 1990).

EXAMPLE 15

4-Acetamidosalicylic acid allyl ester (Xa)

To a stirred suspension of sodium hydride (4.0 g of 60%, 0.1 mmol) in 25 mL DMF was added dropwise a solution of 4-acetamidosalicylic acid (19.5 g, 0.1 mmol) in 50 mL DMF. After the evolution of hydrogen was over, allyl bromide (12.1 g, 0.1 mmol) was added and the mixture was stirred for 8.6 hours. DMF was removed in vacuo and the residue crystallized from methanol/water to give 14.76 g (62.76%) of the title compound as a white solid, mp 156–8° C.

$^1$H-NMR (CDCl$_3$) δ 7.80 (d, 1H), 7.42 (s, 1H), 7.16 (s, 1H), 7.07 (d, 1H), 5.95–6.08 (m, 1H), 5.29–5.44 (m, 2H) 4.80–4.83 (m, 2H), 2.19 (s, 3H).

MS (m/e) 236 corresponds to M+H$^+$.

EXAMPLE 16

N-[4-(Allyloxycarbonyl)-3-(2-nitro-4-trifluoromethylphenoxy)]phenylacetamide (XIIa)

To a stirred suspension of sodium hydride (1.69 of 60%, 42 mmol) in 16 mL DMF was added 4-acetamidoslicylic acid allyl ester (10.0 g, 42 mmol). After the evolution of hydrogen was over, to this was added 4-chloro-3-nitrobenzotrifluoride (9.46 g, 42 mmol) and the mixture heated at reflux for 45 minutes. DMF was removed in vacuo and the residue chromatographed on silica using dichloromethane with 3% methanol as a solvent system, to give 13.0 g (72.95%) of the title compound as a white solid, mp 160°–163° C.

$^1$H-NMR (CDCl$_3$) δ 8.22 (s, 1H), 8.03 (d, 1H), 7.68 (s, 1H), 7.61–7.65 (m, 3H), 7.36 (d, 1H), 6.83 (d, 1H), 5.65–5.78 (m, 1H), 5.10–5.21 (m, 2H), 4.57–4.60 (m, 2H), 2.18 (s, 3H).

MS (m/e) 385 corresponds to M+H$^+$.

EXAMPLE 17

N-[4-(hydroxycarbonyl)-3-(2-nitro-4-trifluoromethylphenoxy)]phenylacetamide (XIIIa)

To a mixture of tris(dibenzylideneacetone)dipalladium (0) (550 mg) and triphenylphosphine (660 mg) was added anhydrous dichloromethane (20 mL) and the mixture stirred for 30 minutes. To this was added N-[4-(allyloxycarbonyl)-3-(2-nitro-4-trifluoromethylphenoxy)]phenylacetamide (20.0 g, 47 mmol) in 200 mL of dichloromethane followed by a solution of potassium salt of 2-ethylhexanoic acid (9.61 g, 57 mmol) in 50 mL of a mixture of ethyl acetate and dichloromethane (3:1). The mixture was stirred for 16 hours and acidified with 75 mL of 1N aqueous HCl. The aqueous layer separated. The organic layer was washed with water, dried and concentrated in vacuo. The residue was triturated with ether to give 14.91 g (82.6%) of the title compound as a white solid. Recrystallization from ether gave a sample whose melting point was 196°–200° C.

$^1$H-NMR (CDCl$_3$) δ 8.06 (s, 1H), 7.86 (d, 1H), 7.61 (s, 1H), 7.49 (d, 1H), 7.36 (d, 1H), 6.75 (d, 1H), 2.01 (s, 3H).

MS (m/e) 385 corresponds to M+H$^+$.

EXAMPLE 18

4-Acetylamido-N-[2-(diethylamino)ethyl]-2-(2-nitro-4-trifluoromethylohenoxy) benzamide (XIVa)

To cold dichloromethane (20 mL) was added oxalyl chloride (432 mg, 3.4 mmol). To this solution was added dropwise, with stirring, a solution of DMF (0.3 mL) in 5 mL dichloromethane. After stirring for another 15 minutes, N-[4-(hydroxycarbonyl)-3-(2-nitro-4-trifluoromethylphenoxy)]phenylacetamide (1.153 g, 3 mmol) was added and the mixture stirred for 30 minutes. To this was added N,N-diethylethylenediamine (415 mg, 3.57 mmol) and triethylamine (460 mg, 4.55 mmol). The mixture was stirred for 1.5 hours at room temperature, washed with aqueous sodium bicarbonate, dried and concentrated in vacuo to give the title compound as an orange solid.

$^1$H-NMR (CDCl$_3$) δ 8.11 (s, 1H), 7.87 (d, 1H), 7.82 (d, 1H), 7.63 (s, 1H), 7.03 (s, 1H), 6.72 (d, 1H), 6.64 (d, 1H), 2.60–2.80 (m, 2H), 2.35–2.55 (m, 6H), 2.08 (s, 3H), 0.89 (t, 6H).

MS (m/e) 483 corresponds to M+H$^+$.

EXAMPLE 19

Biological Assay

Cell Culture: HCT116/VM46 cells were selected from human colon carcinoma HCT116 cell line for resistance to VM26 and MCF-7/ADR cells were selected from human breast carcinoma MCF-7 cell line for resistance to Adriamycin. Both cell types exhibit MDR phenotype and overexpress high levels of MDR-1 mRNA. The cell lines were grown in tissue culture flasks containing McCoy's A medium and 10% fetal bovine serum. Cells were maintained at 37° C. in a humidified atmosphere containing 5% CO$_2$ and subcultured every 5 days.

Cytotoxic Assay: The cells were seeded in 96 well microtiter plates at 5×10$^3$ cells per well and allowed to grow for 24 hours at 37° C. Cells were then incubated with decreasing amounts of antitumor agents: Adriamycin (100 μM, maximal concentration) or actinomycin D (17.6 ng/ml), for MCF-7 and HCT-116 cells, respectively. Chemosensitizers were added at variable concentrations ranging from 0.08 μM to 40 μM. In parallel, verapamil was used as positive control at the same concentrations. After 48 hours of incubation, the cells were washed, fixed and stained with crystal violet. Absorbance was read by Molecular Devices' microtiter plate reader at the wavelength of 595nM. The IC$_{50}$ value (50% inhibition of cell growth) was determined from relative survival rates resulted from two to three independent experiments. The term "fold resistance" was defined as the ratio of the IC$_{50}$ for antitumor drug in the presence or absence of chemosensitizer in resistant cells divided by the IC$_{50}$ for antitumor drug in its sensitive counterpart. This value provides an estimate of the apparent potency of each reversing agent in enhancing drug effect.

Table I and II show a few representative chemosensitizers of the instant invention which showed higher MDR reversing activity compared to that of verapamil in human colon carcinoma HCT-116 resistant cells and in human breast carcinoma MCF-7 resistant cells, respectively.

TABLE I

| MDR Reversing Effects of Chemosensitizers In Human Colon Carcinoma HCT-116 Cells | | | |
|---|---|---|---|
| Cell Line | Compound | ActD IC$_{50}$ (ng/ml) | Fold Resistance |
| | (0.24 μM) | | |
| HCT116 | — | 0.5 | 1.0 |
| HCT-116/VM46 | — | 8.9 | 15.6 |
| HCT-116/VM46 | In | 1.2 | 2.4 |
| HCT-116/VM46 | Ik | 1.2 | 2.4 |
| HCT-116/VM46 | Im | 1.4 | 2.8 |
| HCT-116/VM46 | Ih | 1.4 | 2.8 |

TABLE I-continued

MDR Reversing Effects of Chemosensitizers In Human Colon Carcinoma HCT-116 Cells

| Cell Line | Compound | ActD IC$_{50}$ (ng/ml) | Fold Resistance |
|---|---|---|---|
| HCT-116/VM46 | Ip (0.4 μM) | 1.7 | 3.4 |
| HCT116 | — | 0.5 | 1.0 |
| HCT-116/VM46 | — | 1.0 | 20.0 |
| HCT-116/VM46 | Id | 1.2 | 2.4 |
| HCT-116/VM46 | If | 1.6 | 3.2 |
| HCT-116/VM46 | Ij | 1.6 | 3.2 |
| HCT-116/VM46 | Ii | 1.7 | 3.4 |
| HCT-116/VM46 | Io | 1.8 | 3.6 |
| HCT-116/VM46 | Ig | 2.0 | 4.0 |
| HCT-116/VM46 | Ie | 2.5 | 5.0 |
| HCT-116/VM46 | Ib | 3.0 | 6.0 |
| HCT-116/VM46 | Verapamil | 5.8 | 11.6 |

TABLE II

MDR Reversing Effects of Chemosensitizers in Human Breast Carcinoma MCF-7 Cells

| Cell Line | Compound | ADR IC$_{50}$ (μM) | Fold Resistance |
|---|---|---|---|
| MCF-7 | — (0.24 μM) | 0.36 | 1 |
| MCF-7/ADR | — | 50 | 138.9 |
| MCF-7/ADR | In | <2 | <5.6 |
| MCF-7/ADR | Ik | 3.7 | 10.3 |
| MCF-7/ADR | Im | 4.8 | 13.3 |
| MCF-7/ADR | Ij (0.67 μM) | 7.0 | 19.4 |
| MCF-7/ADR | Ih | 10.0 | 27.8 |
| MCF-7/ADR | Ii | 10.4 | 28.9 |
| MCF-7/ADR | If | 11.4 | 31.7 |
| MCF-7/ADR | Ig | 14.3 | 39.7 |
| MCF-7/ADR | Id | 23 | 63.9 |
| MCF-7/ADR | Verapamil | 23 | 63.9 |

The foregoing tests revealed that the compounds of the instant invention are useful for the reversal of MDR to anti-cancer drugs. Thus this invention also relates to the use of compound of formula I as agents for adjuvant chemotherapy for neoplasias resistant to multiple drugs.

Compounds of formula I may form pharmaceutically acceptable acid addition salts. Said salts are those in which anion does not contribute significantly to the toxicity of the salt and are compatible with the customary pharmaceutical vehicles and adapted for oral or parenteral administration. The pharmaceutically acceptable acid addition salts include the salts of compounds of formula I with mineral acids such as hydrochloric acid, hydrobromic acid, phosphoric acid and sulfuric acid; with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, isethionic acid, p-tolenesulfonic acid and other acids known and used in the galenic pharmacy. Thus this invention further relates to a pharmaceutically acceptable salt of a compound of formula I.

The mode of systemic administration, dosage, and dosage regimen must in each case be carefully adjusted by utilization of sound professional judgment and consideration of the age, weight and condition of the recipient. Generally, the daily dose will be from about 0.1 g to about 10 g, preferably 0.5 g to 5 g, when given orally. In some instances, a sufficient therapeutic effect can be obtained at lower doses while in others, larger doses will be required. As is apparent to one skilled in clinical pharmacology, the amount of a formula I compound comprising the daily dose may be given in a single or divided dose, taking into account those principles understood by the skilled practitioner and necessary for his practice of the art.

The term "systemic administration" as used herein refers to oral, sublingual, buccal, nasal, dermal, rectal, intramuscular, intravenous, and subcutaneous routes. Generally, it will be found that should a compound of the present invention is administered orally, a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical formulations comprised of an effective MDR reversal amount of a compound of formula I or a pharmaceutically acceptable acid addition salt thereof and a pharmaceutically acceptable carrier. Pharmaceutical formulations for effecting such treatment will contain a major or minor amount (e.g. from 95% to 0.5%) of at least one compound of the present invention in combination with pharmaceutical carrier, the carrier comprising one or more solid, semi-solid, or liquid diluent, filler and formulation adjutant which is non-toxic, inert and pharmaceutically acceptable. Such pharmaceutical formulations are preferably in dosage unit forms; i.e. physically discrete units having a predetermined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the pre-determined dosage regimen, usually a whole, half, third, or less of the daily dose administered once, twice, three or more times a day. It is envisioned that other therapeutic agents can also be present in such a formulation. Pharmaceutical formulations which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral formulations are in the form of tablets, capsules, and may contain conventional excipients such as binding agents, (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of the active comound in water or a vehicle consisting of a polyhydric aliphatic alcohol such a glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

What is claimed is:

1. A compound of formula I or a pharmaceutically acceptable salt thereof

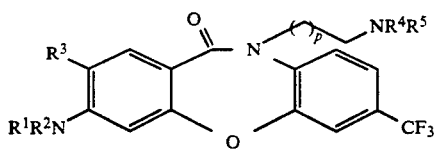

wherein p is 1 to 3;

$R^1$ and $R^2$ each are independently hydrogen or an acyl group $R^6CO—$, in which $R^6$ is $C_{1-6}$ alkyl, $C_{3-7}$ cycloalkyl, $C_{2-7}$ alkenyl, aryl where aryl is phenyl or phenyl independently substituted with one to three halogen, $C_{1-6}$alkyl, $C_{1-6}$alkoxy or $C_{1-6}$alkoxy or $C_{1-6}$ alkylthio or radical of the formula

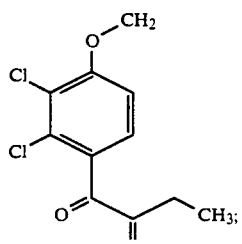

$R^3$ is hydrogen or chloro;

$R^4$ and $R^5$ each are independently $C_{1-6}$ alkyl.

2. A compound of formula I in which p equals 1 and $R^6CO—$ is a radical selected from

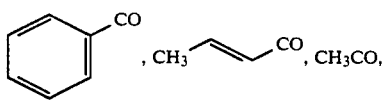

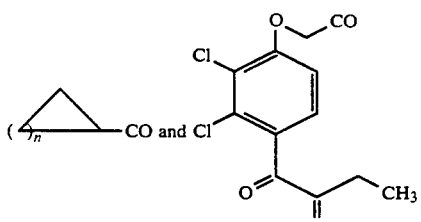

in which n is 1 to 4.

3. The compound of claim 2 that is N-[2-chloro-10,11-dihydro-10-[2-(diethylamino) ethyl]-11-oxo-7-(trifluoromethyl) -dibenz[b,f][1,4]oxazepin-3-yl]benzamide.

4. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]crotonamide.

5. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]propionamide.

6. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]cyclopropanecarboxamide.

7. The compound of claim 2 that is N-[2-chloro-10,11-dihydro-10-[2-(diethylamino) ethyl]-11-oxo-7-(trifluoromethyl) dibenz[b,f][1,4]oxezpin-3-yl]-2-methylpropionamide.

8. The compound of claim 2 that is N-[2-chloro-10,11-dihydro-10-[2-(diethylamino) ethyl]-11-oxo-7-(trifluoromethyl) dibenz[b,f][1,4]oxezpin-3-yl]cyclobutanecarboxamide.

9. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]cyclohexacarboxamide.

10. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]-N-(cycloheptylcarbonyl) cycloheptanecarboxamide.

11. The compound of claim 2 that is N-[2-chloro-10, 11-dihydro-10-[2-(diethylamino) ethyl]-11-oxo-7-(trifluoromethyl) dibenz[b,f][1,4]oxazepin-3-yl]-cycloheptanecarboxylate.

12. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]etacrynylamide.

13. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]cyclopentanecarboxamide.

14. The compound of claim 2 that is N-[2-chloro-10,11-dihydro-10-[2-(diethylamino) ethyl]-11-oxo-7-(trifluoromethyl) dibenz[b,f][1,4]oxazepin-3-yl]acetamide.

15. The compound of claim 2 that is N-[10,11-dihydro-10-[2-(diethylamino) ethyl]-11-oxo-7-(trifluoromethyl)-dibenz[b,f][1,4]oxazepin-3-yl]acetamide.

16. A pharmaceutical formulation which comprises as an active ingredient a multidrug resistant amount of a compound of formula I, as claimed in any one of claims 1 to 15, associated with one or more pharmaceutically acceptable carriers, excipients and diluents therefor.

17. A method of reversing multidrug resistance of cancer cells to a cytotoxic drug during chemotherapy, which comprises administering a multidrug resistance reversal effective amount of a compound of formula I as claimed in any one of claims 1 to 15, or a pharmaceutically acceptable salt thereof, to a patient having the multidrug resistant cancer cells.

* * * * *